United States Patent [19]

Narayanan et al.

[11] Patent Number: 5,262,449
[45] Date of Patent: Nov. 16, 1993

[54] RADIATION CURABLE COATING COMPOSITIONS

[75] Inventors: Kolazi S. Narayanan, Palisades Park, N.J.; Jeffrey S. Plotkin, Monsey, N.Y.; Fulvio J. Vara, Chester; James A. Dougherty, Pequannock, both of N.J.

[73] Assignee: ISP Investments Inc., Wilmington, Del.

[21] Appl. No.: 936,470

[22] Filed: Aug. 28, 1992

Related U.S. Application Data

[63] Continuation of Ser. No. 579,512, Sep. 10, 1990, abandoned.

[51] Int. Cl.$^5$ .......................... C08F 2/50; C08F 16/18; C08F 16/32; C08F 24/00
[52] U.S. Cl. ........................................ 522/31; 522/96; 522/103; 522/169; 526/269; 427/517
[58] Field of Search ................... 522/169, 31, 96, 103; 526/269; 528/370; 427/517

[56] References Cited

U.S. PATENT DOCUMENTS

| | | | |
|---|---|---|---|
| 2,522,680 | 9/1950 | Kropa | 549/229 |
| 3,249,631 | 5/1966 | Soffer | 522/169 |
| 3,422,118 | 1/1969 | Hostettler | 526/269 |
| 3,532,715 | 10/1970 | Hostettler | 526/269 |
| 4,058,400 | 11/1977 | Crivello | 522/31 |
| 4,108,747 | 8/1978 | Crivello | 522/170 |
| 4,245,029 | 1/1981 | Crivello | 522/31 |
| 4,273,668 | 6/1981 | Crivello | 522/31 |
| 4,314,945 | 2/1982 | McMullen | 549/230 |
| 4,634,722 | 1/1987 | Gallop | 526/269 |
| 4,885,319 | 12/1989 | Dougherty | 522/31 |

OTHER PUBLICATIONS

Derwent Abstract 76-31371 x/17 May 1976 Trofimov et al.
Chemical Abstracts vol. 82, 1975, p. 368, Abstract No. 4231s "Vinyl Ethers" Trofimov.

*Primary Examiner*—Roland Martin
*Assistant Examiner*—A. H. Koeckert
*Attorney, Agent, or Firm*—Marilyn J. Maue; Joshua J. Ward

[57] ABSTRACT

This invention relates to a coating composition which can be cured by exposure to radiation energy in the presence of a cationic photoinitiator. The composition comprises a mixture of between about 1 and about 75 wt. % of a reactive vinyl or alk-1-enyl ether cyclocarbonate having the formula

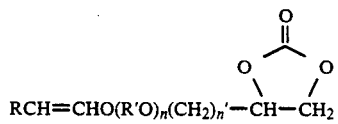

$$RCH=CHO(R'O)_n(CH_2)_{n'}-CH-CH_2$$

wherein R is hydrogen or lower alkyl; R' is $C_2$ to $C_4$ alkylene; n has a value of from 0 to 4 and n' has a value of from 1 to 4 and between about 99 and about 25 wt. % of a polymerizable compound containing an onium salt initiator which is normally insoluble in said polymerizable compound or a mixture thereof. The invention also relates to the use of the composition as a protective coating on a substrate.

12 Claims, No Drawings

RADIATION CURABLE COATING COMPOSITIONS

This is a continuation of application Ser. No. 579,512, filed Sep. 10, 1990, now abandoned.

In one aspect, the invention relates to a novel coating composition which is cationically curable in the presence of an onium salt initiator.

In another aspect, the invention relates to the process of applying said composition on a substrate and curing said composition to a hard, durable protective coating by exposure to a source of radiant energy.

BACKGROUND OF THE INVENTION

It is known that acrylate containing coating materials can be cured either thermally or by radiation in the presence of a free radical photoinitiator. However, it is well recognized that thermal curing is not cost efficient and that radiation curing in free radical systems is oxygen inhibited, usually requiring an inert atmosphere or the addition of a hydrogen donating component. It has been found that polymerization or curing in free radical systems ceases almost immediately upon removal from the source of radiation; thus, the cured product often contains significant amounts of unpolymerized components in a discontinuous protective coating. Although epoxides and vinyl ethers are known to cure by cationic polymerization in the presence of onium salt initiators, these initiators, being salts are difficult to solubilize and thus the choice of suitable reactive diluents is greatly restricted. The choice of suitable reactive diluent may be increased by incorporation of appropriate solvents into the coating formulation. However the addition of non-reactive diluents with low volatility in the formulation adversely affect the coating properties. Accordingly, it is an aim of research to develop monomers which provide stable formulations with the above polymerizable materials and which solubilize the cationic initiator in order to promote radiation induced cationic polymerization and to incorporate the beneficial properties of the vinyl ethers, epoxides, acrylates or urethanes into the finished product. Additionally it is desirable that such monomers or their oligomers be amenable to radiation curing at a rapid rate under mild temperature conditions in an onium salt initiated polymerization which is not oxygen inhibited and which permits continued polymerization after removal from the source of radiation exposure. It is further desired that the reactive monomer be capable of minimizing undesirable properties of certain coating materials, such as the acrylate monomers which are known skin irritants and that it also serve as a solvent for the initiator.

Accordingly, it is an object of this invention to provide a reactive diluent for cationically induced radiation polymerizations of polymerizable monomers and oligomers normally not polymerized in cationic systems due to their incompatibility with onium salt photoinitiators.

Another object of this invention is to provide a solvent for an onium salt photoinitiator which is economically and conveniently prepared from commercially available compounds.

Another object is to provide a mono-functional reactive diluent capable of modifying cross-linked density and flexibility of the resulting polymerized coatings.

Another object is to provide an onium salt photoinitiator diluent which is incorporated into the cured product of a radiation curable resin.

Still other objects are to provide a process for coating a substrate with an improved protective coating and to provide a substrate which is highly resistant to abrasion and chemical attack.

These and other objects of this invention will become apparent from the following description and disclosure.

THE INVENTION

In accordance with this invention there is provided a cationically induced radiation polymerizable composition which comprises a mixture of (a) between about 1 and about 75 wt. % of a reactive vinyl or alk-1-enyl ether cyclocarbonate having the formula

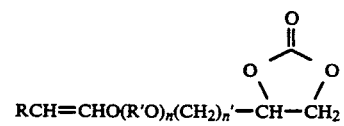

wherein R is hydrogen or lower alkyl; R' is $C_2$ to $C_4$ alkylene; n has a value of from 0 to 4 and n' has a value of from 1 to 4 and (b) between about 99 and about 25 wt. % of a coreactant monomer and/or oligomer which mixture additionally contains between about 0.5 and about 5% of a cationic onium salt initiator.

Component (b) of the composition can be a monomer or oligomer in which an onium salt is normally insoluble or sparingly soluble such as vinyl ether monomers and oligomers alkyl monovinyl ethers or alkyl monoalk-1-enyl ethers, the divinyl ether of cyclohexane dimethanol, a vinyl ether capped urethane or an ester and the like. Component (b) can also be a monomer or oligomer of an epoxide, e.g. bisphenol A diepoxide, a Novolac resin, and the like. Acrylates or methacrylates can also be employed as component (b) alone or in admixture with any of the aforementioned comonomers; however, these comonomers require a hybrid curing system of onium salt and free radical initiator.

The preferred compositions of the present invention are those wherein n of component (a) has a value of zero, n' has a value of one and R is hydrogen or methyl and component (b) is a divinyl ether terminated compound, most preferably, dimethyl cyclohexyl divinyl ether, mixed with a vinyl ether or epoxide capped oligomer. The mole ratio of component (a) to component (b) in the mixture can vary within a wide range; however, an excess of component (b), e.g. a ratio of between about 1:20 and about 1:2 is recommended.

It has been found that the present compounds of component (a), having a vinyl or alk-1-enyl ether terminal group bonded directly or indirectly to the alkyl cyclocarbonate group, provide excellent solubilizing properties for the cationic initiators resulting in stable liquid initiator containing solutions. Also the vinyl or alk-1-enyl ether terminated cyclocarbonates are capable of interacting with polymerizable monomers and oligomers of component (b) to form non-yellowing, branched coatings of high resistance to abrasion and chemical attack. Unsubstituted cyclocarbonates and alkyl or polyether substituted cyclocarbonates do not share these properties since they fail to react with polymerizable monomers and oligomers. It has also been found that polyether compounds, which have been used to solubilize onium initiators, cause yellowing in the finished product and are therefore objectionable for many uses. The present vinyl or alk-1-enyl ether cyclocarbonates are superior solubilizers, do not cause yellowing and can be used in much smaller amounts to provide a stable liquid initiator solution. However, because the vinyl or alk-1-enyl ether cyclocarbonates of the present invention are multi-functional, i.e. excellent solvents for the difficultly solubilizable cationic initiators and reactive monomers with the monomers or oligomers of component (b) they can be used in substantially large amounts to alter properties in the cured product and to replace the conventional non-reactive initiator solvents, e.g. butyrolactone or propylene carbonate, and other solvents commonly employed in prior cationic systems. Prior initiator solvents were generally employed in low concentrations since their non-polymerizable nature causes tacky areas and discontinuous coating or blistering which can lead to rupture in the finally cured coating.

The vinyl or alk-1-enyl ether cyclocarbonates can be prepared directly by the addition of carbon dioxide to the corresponding vinyl or alk-1-enyl glycidyl ether, in the presence of phase transfer catalysts, such as tetrabutyl ammonium bromide or iodide, tetraethyl ammonium bromide or iodide and cyclic ethers such as 18 crown 6 ether with potassium iodide. The reaction is generally run under pressure ranging from 50 to 1000 psig. at a temperature of from 50° C. to 150° C. for a period of from one hour to 24 hours and the product isolated by distillation.

The alk-2-enyl ether cyclocarbonates can also be prepared by reacting an alk-2-enyl ether diol with a dialkyl carbonate in the presence of a base catalyst such as sodium or potassium methoxide or butoxide, sodium or potassium hydroxide or sodium or potassium metal. As the reaction proceeds the evolving alkanol is distilled out of the system as an azeotrope along with some of the dialkyl carbonate and make-up dialkyl carbonate is continuously added. The temperature for this reaction can vary between about 70° and 100° C. and reaction time is typically between 1 and 8 hours. The product is then isolated by vacuum distillation. Alternatively the alk-2-enyl ether cyclocarbonates can be prepared by addition of carbon dioxide to alk-2-enyl glycidyl ethers using the conditions described above.

The alk-1-enyl ether cyclocarbonates, where R is lower alkyl, can be prepared by first synthesizing a alk-2-enyl ether cyclocarbonate as described above and isomerizing it to the corresponding alk-1-enyl ether. Pure alk-2-enyl ether cyclocarbonate is catalytically isomerized to the corresponding alk-1-enyl ether by heating in the presence of known, isomerization catalysts, such as $RuCl_3.H_2O$, $H_2Ru(PPh_3)_4$, $Cl_2Ru(PPh_3)_4$, rhodium chloride, palladium acetate, palladium on carbon or alumin, or ruthenium on alumina or carbon. Isomerization temperatures range from about 100° C. to about 180° C. Higher than 99% isomerization can be achieved in one to several hours when a homogeneous catalyst is employed, while several hours to one day is required when a heterogeneous catalyst is used. Solvents are optionally used in this reaction. The selective preparation of either the prop-1-enyl ether cyclocarbonate or the prop-2-enyl ether cyclocarbonate or a precise mixture of the prop-1-enyl- and prop-2-enyl- ether compounds is disclosed in copending U.S. patent application Ser. No. FDN-1861/B now U.S. Pat. No. 5,045,124.

Examples of suitable cationic initiators include the onium salt initiators such as the triphenyl sulfonium salt of phosphorous hexafluoride, diphenyl iodium salt, tetrazolium chloride, phenyl onium salts or aryl alkyl onium salts, etc. described by M. J. M. Abadie, Advantages and Development of Photochemical Initiators, in the European Coatings Journal 5/1988, pages 350-358. Also, mixtures of the present cationic initiators with up to 60% of free radical photoinitiators can be employed as the photoinitiator, if desired.

Specific examples of suitable monomers and oligomers used in the above composition include the divinyl ether of tripropylene glycol, dimethyl cyclohexyl divinyl ether, hexanediol divinyl ether, hexadecyl monovinyl ether, vinyl ether terminated urethanes, diglycidyl ethers of bisphenol A, novolac epoxy resins, Epon resins, epoxy acrylate resins, acrylate urethane resins and oligomers of the above monomers as well as mixtures of the above monomers and/or oligomers.

The present compositions are easily prepared by forming a slurry of cationic initiator preferably in a concentration of from about 1 to about 3 wt. % in liquid component (b) or a solution of component (b). Component (a) in the desired amount is slowly added to the slurry with continued stirring until a clear solution is obtained. This procedure is normally carried out under about ambient conditions; although elevated temperatures up to about 100° C. and pressure up to about 50 psig. can be employed when desired.

Optional adjuvants may be added to the composition to supply additional wetting characteristics. Suitable wetting agents include fluorinated alkyl ester surfactants, ethoxylates of alkyl phenols, fatty alcohols and alpha-olefins.

The above composition are suitable for coating on a substrate such as glass, ceramic, wood, plastic, metal, leather, paper and the like in a thickness of from about 0.1 to about 5 mils.

Curing of the present compositions can be effected in less than 1 second by exposure to a source of radiation, e.g. between about 100 and about 800 millijoules/$cm^2$ of UV light, between about 0.5 and about 5 megarads of electron beam exposure or equivalent radiation exposures of gamma ray, X-ray, etc. Laser emissions can also be employed to effect curing.

The general techniques for exposing coating surfaces to radiation for curing are well known and the present compositions are cured in a conventional manner.

Having thus described the invention, reference is now had to the following Examples which illustrate specific and preferred embodiments, but which are not to be construed as limiting to the scope of the invention as more broadly described above and in the appended claims.

EXAMPLE 1

A. To a 4 dram vial containing 2.5 g. of liquid divinyl ether of triethylene glycol (RAPICURE DVE-3 [1]) was added 5 ml of FX-512 [2], i.e. a mixture of aryl sulfonium salts of hexafluorophosphate. The 20% solution was then blended with RAPICURE DVE-3 and RAPICURE CHVE, (i.e. the divinyl ether of 1,4-cyclohexane dimethanol) [3] to reduce the FX-512 initiator concentration to 2%. The percent of RAPICURE DVE-3 required to solubilize 2% initiator in RAPICURE CHVE is reported in following Table I.

B. Part A was repeated except that the prop-1-enyl ether of propylene carbonate (PEPC) was substituted for RAPICURE DVE-3. The percent of PEPC required to solubilize 2% initiator in RAPICURE CHVE is also reported in following Table I.

TABLE I

% of DVE-3 or PEPC needed
to Solubilize 2% FX-512 in RAPICURE CHVE

| Comp. | | |
|---|---|---|
| A | DVE-3 | 78 |
| B | PEPC | 23 |

(1) Supplied by GAF Chemicals Corp.
(2) Supplied by Minnesota Mining and Mfg. Co.
(3) Supplied by GAF Chemicals Corporation Upon curing coatings using EPON-828 (diepoxide of bisphenol A resin) as the polymerizable oligomer in above systems A and B, a yellowish product was produced by coating A; whereas no color development occurred with coating B.

EXAMPLE 2

To a 4 ounce amber colored bottle was added 25 g. of vinyl ether terminated urethane oligomer i.e. Vectomer 2020 (4) and 25 g. of RAPICURE CHVE at a temperature of 45° C. with constant agitation. After a uniformly blended liquid mixture was obtained, 0.25 g. of a fluorinated alkyl ester surfactant (Fluorad 171 (2)) and 2 g. of FX-512 initiator were added and mixed therein at 45° C. The resultant formulation is designated Sample 2.

EXAMPLE 3

The procedure of Example 2 was repeated except that 5 g. of PEPC was substituted for 5 g. of the 25 g. of RAPICURE CHVE. The resultant formulation is designated Sample 3.

(4) Supplied by Allied Signal Corp.

EXAMPLE 4

The procedure of Example 2 was repeated except that 5 g. of RAPICURE DVE-3 was replaced for 5 g. of RAPICURE CHVE. The resultant liquid is designated Sample 4.

EXAMPLE 5

To a 4 ounce amber colored bottle was added 25 g. of acrylate terminated epoxy oligomer such as Ebacryl 6700 from RadTech Specialties, 20 g. of RAPICURE CHVE and 5 g. of PEPC at temperature of 45° with constant agitation. After a uniformly blended liquid was obtained, a hybrid initiator mixture of 1 g. of FX-512 cationic photoinitiator and phenyl-1-hydroxy cyclohexane ketone free radical initiator (Irgacure 184, supplied by Ciba-Giegy), together with 0.25 g. of Fluorad 171, were added and mixed at 45° for 20 minutes. The resultant formulation was designated as Sample 5.

EXAMPLE 6

To a 4 ounce amber colored bottle was added 25 g. of bisphenol A diepoxide having a molecular weight of 500 to 560, Epon 1001, 20 g. RAPICURE CHVE and 5 g. of PEPC at a temperature of 45° C. with constant agitation. After a uniformly blended liquid is obtained, 0.25 g. of Fluorad 171 and 1 g. of FX-512 were added and mixed at 45° C. for 20 minutes. The resultant formulation was designated as Sample 6.

EXAMPLE 7

To a 4 ounce amber colored bottle was added 25 g. of bisphenol A diepoxide having a molecular weight of 500 to 560, Epon 1001 and 25 g. of RAPICURE CHVE at a temperature of 45° C. with constant agitation. After a uniformly blended liquid is obtained, 0.25 g. of Fluorad 171 and 1 g. of FX-512 were added and mixed at 45° C. for 20 minutes. The resultant formulation was designated as Sample 7.

EXAMPLE 8

To a 4 ounce amber colored bottle was added 25 g. of bisphenol A diepoxide having a molecular weight of 370 to 384, Epon 825 and 25 g. of RAPICURE CHVE at a temperature of 45° C. with constant agitation. After a uniformly blended liquid is obtained, 0.25 g. of Fluorad 171 and 1 g. of FX-512 were added and mixed at 45° C. for 20 minutes. The resultant formulation was designated as Sample 8.

EXAMPLE 9

The procedure for Example 8 was repeated except that 5 g. of RAPICURE CHVE was replaced with 5 g. of PEPC. The resultant formulation was designated as Sample 9.

Each of the above samples were examined for clarity of the solution Samples 2, 4 and 7 were cloudy; whereas Sample 3, 5, 6, 8 and 9 were clear. These samples were individually coated on aluminum panels by hand draw downs using a 12 Mayer bar to give a coating thickness of about 1.0 microns. The corresponding panels 2-9 were then subjected to a UV light exposure at 15 joules/cm$^2$ by passing them under two 200 watt/inch medium pressure mercury vapor lamps at 100 feet/minute and then tested for solvent resistance, release impact and elongation For the solvent resistance test, a methylethyl ketone saturated cheesecloth was rubbed across the surface of the coated panel under a constant pressure. The number of back and forth strokes needed to break through the coating was recorded. The reverse impact test was carried out by placing a coated panel face down on a die containing a 0.640 inch hole. A 0.625 inch pin with rounded tip was placed on the back of the panel directly over the hole. A 1 lb. weight was dropped, from varying heights, onto the pin causing rapid deformation of the panel and coating and the coating was examined for cracking or crazing. The maximum energy the coating can absorb before failure was recorded. The results of these tests are reported in following Table II.

TABLE II

| FILM PROPERTIES (film thickness 25 um) | | | | | | | | |
|---|---|---|---|---|---|---|---|---|
| | SAMPLES | | | | | | | |
| | 2 | 3 | 4 | 5 | 6 | 7 | 8 | 9 |
| MEK DOUBLE RUBS (ASTM D882) | 0 | >100 | 0 | >100 | >100 | 0 | >100 | >100 |
| Reverse Impact | — | >160 | — | 70 | 120 | — | 80 | >160 |
| Elongation | — | 50 | — | 10 | 20 | — | 10 | 30 |

It is to be understood that other reactive diluents of this invention can be substituted in Example 4 or in Example 6 or in Example 8 to provide clear initiator solutions and cured compositions which are chemically

What is claimed is:

1. A coating composition rapidly curable by exposure to a source of radiation which consists essentially of a cationically copolymerizable mixture of
   (a) between about 1 and about 75 wt. % of a polymerizable vinyl or alk-1-enyl ether cyclocarbonate having the formula

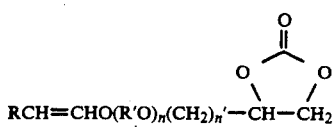

wherein R is hydrogen or lower alkyl; R' is $C_2$ to $C_4$ alkylene; n has a value of from 0 to 4 and n' has a value of from 1 to 4 and
   (b) between about 99 and about 25 wt. % of a at least one copolymerizable compound which is capable of copolymerizing with (a), the mixture containing in solution between about 1 and about 5 wt. % of a cationic onium salt initiator which is solubilized by (a).

2. The coating composition of claim 1 in which component (b) is a compound in which the onium salt is normally insoluble.

3. The coating composition of claim 1 wherein n' has a value of one and n is zero.

4. The coating composition of claim 1 wherein said onium salt initiator is the triphenyl sulfonium salt of phosphorous hexafluoride.

5. The coating composition of claim 1 wherein said copolymerizable compound is a monomer or oligomer selected from the group of a vinyl ether, an alk-1-enyl ether, an epoxide, an acrylate, a methacrylate, a vinyl ether urethane, a vinyl lactam or a combination thereof.

6. The coating composition of claim 1 wherein said component (b) is divinyl ether of tripropylene glycol.

7. The coating composition of claim 1, 2, 3 or 4 wherein said component (b) is 1,4-dimethylcyclohexyl divinyl ether.

8. The coating composition of claim 1, 2, 3 or 4 wherein component (b) is a mixture of 1,4-dimethylcyclohexyl divinyl ether and a vinyl ether terminated urethane oligomer.

9. The coating composition of claim 1, 2, 3 or 4 wherein component (a) is

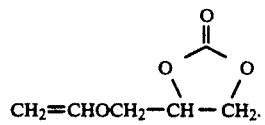

10. The coating composition of claim 1, 2, 3 or 4 wherein component (a) is

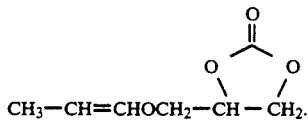

11. The process which comprises coating the surface of a substrate with a protective amount of the composition of claims 1 or 2 and irradiating said coated surface to cure and adhere said composition on said substrate.

12. A substrate coated with a protective layer of the composition of claims 1 or 2 in a cured or uncured state.